United States Patent [19]

Sullivan

[11] Patent Number: 5,078,308

[45] Date of Patent: Jan. 7, 1992

[54] DEVICE TO APPLY ELASTIC GLOVES

[76] Inventor: John L. Sullivan, P.O. Box 6379, Incline Village, Nev. 89450

[21] Appl. No.: 656,793

[22] Filed: Feb. 19, 1991

[51] Int. Cl.⁵ .............................................. A47G 25/90
[52] U.S. Cl. ..................................... 223/111; 206/278
[58] Field of Search ............... 223/111; 206/278, 438; 2/168, DIG. 7

[56] References Cited

U.S. PATENT DOCUMENTS

| | | | |
|---|---|---|---|
| 1,938,685 | 12/1933 | Breulis et al. | 223/111 |
| 3,067,001 | 12/1962 | McCollum | 223/111 X |
| 3,695,493 | 10/1972 | Karr . | |
| 4,002,276 | 1/1977 | Poncy et al. | 223/111 |
| 4,069,913 | 1/1978 | Harrigan | 223/111 X |
| 4,228,935 | 10/1980 | Madray . | |
| 4,889,266 | 12/1989 | Wight | 223/111 |
| 4,898,309 | 2/1990 | Fischer . | |
| 4,915,272 | 4/1990 | Vlock . | |

Primary Examiner—Werner H. Schroeder
Assistant Examiner—Bibhu Mohanty

[57] ABSTRACT

A simplified glove donning device to inflate and detect pinhole size leaks in elastic gloves using no internal or external energy sources. The device may be mounted to any flat surface. Glove donning cylinders (100) hold elastic gloves securely in place and forms an air tight seal between cylinder (100) and elastic glove. When a hand is inserted into the cylinder (100), sealed with an elastic glove, air in the cylinder is forced out through a one-way check valve (400). When the hand is retracted slightly or fully, the elastic glove is pulled into the cylinder (100) by the vacuum developed below the glove, thus, it expands larger than a hand. The user may then insert a hand friction free and disengages the glove from the cylinder (100) by rolling the cuff up and off the upper edge (130) of the cylinder (100). When the air tight seal is broken, the glove deflates rapidly and conforms to the shape of the hand with no air pockets at the finger tips. If the vacuum indicator (500) indicates a loss of vacuum in the cylinder (100), the glove may have a hole through which bodily fluids can pass.

15 Claims, 4 Drawing Sheets

DEVICE TO APPLY ELASTIC GLOVES

BACKGROUND

1. Field of Invention

This invention relates to a device used to apply elastic gloves and detect pinhole size leaks in elastic gloves especially those used by health care professionals.

2. Description of Prior Art

Increasingly, health care professionals wear elastic examination gloves to prevent bodily fluids from passing between patient and care giver. Such precautions may reduce the risk of contracting diseases such as acquired immune deficiency syndrome (AIDS). Some individuals wear two or more pair of gloves on each hand to prevent contaminated bodily fluids from passing through pinhole size voids in the glove material. Dentists may apply up to 100 gloves daily, especially when circulating between more than one patient treatment room. Each time a different patient is to be treated, a pair of gloves must be donned.

These elastic gloves generally assume a "skin tight" fit when worn and are consequently annoying and perhaps difficult to apply, especially if the hand or glove is damp. Air pockets may form at the finger tips requiring several adjustments to release this trapped air. Users who must change gloves frequently, consider glove donning a time consuming, somewhat irritating procedure. The inconvenience of manually donning gloves may actually deter some individuals from using examination gloves.

Without the aid of a device to assist in donning gloves, a person must pick a glove from a box; shake it out; orient the glove; pull it on the hand; and make several gestures to achieve a snug fit and release trapped air at the finger tips. This having been done, the wearer has no way to tell if the glove has tiny voids through which contaminated fluids can pass. Some health care professionals wear two gloves on each hand to protect against fluids leaking through small holes in the elastic material even though this reduces the sense of feel from the fingers and causes more hand fatigue and heat.

Inventors have created several glove donning devices to assist persons in applying elastic gloves. U.S. Pat. No. 4,915,272 to Vlock (1990) discloses a complex device to don and remove elastic gloves while making no attempt to detect small leaks in the glove. The device consists of cylinders, special rims, pivots, pumps, switches, air hose, controls, foot pedal, electrical energy supply, and more. The complexity and cost make this device unsuitable for wide use. Weight, size, and need for external power limits usefulness in some environments. U.S. Pat. No. 3,695,493 to Karr (1972) discloses a less complex device than Vlock's and consists of cylinders, vacuum chambers, rim seals, springs, bellows, valves, and foot treadle. Again, no attempt to detect minute leaks in the glove is made. The foot operated bellows limits where the device may be mounted. Other types of less complex elastic glove donning devices have been disclosed—for example, in U.S. Pat. No. 4,898,309 to Fischer (1990), and U.S. Pat. No. 4,228,935 to Madray (1980). Although inexpensive and having few components, neither attempts to detect leaks nor do they attempt to inflate the elastic glove to reduce friction between hand and glove. These devices merely hold gloves by the cuff.

Considering the foregoing, the art of donning elastic gloves would be advanced by providing a glove donning apparatus allowing easy and unassisted application of elastic gloves. It would be a further advance in the art to provide a glove donning device that detects the presence of pinhole size voids in the glove material through which contaminated fluids might pass to the wearer. This on-site detection of holes in examination gloves may eliminate the need for double glove wearing and contribute to reducing the chance of contaminated bodily fluids causing infection to the health care professional.

Most wearers and potential wearers of elastic gloves who must change gloves several times an hour would prefer a simple, maintenance-free device that needs no power of any kind to operate; that needs no connection to existing equipment; that holds and expands an elastic glove to reduce friction against the hand, and quickly aids in detecting small holes in the glove.

OBJECTS AND ADVANTAGES

In consideration of the present state of the art, the primary objects of the invention are:

(a) to provide a device for easily, conveniently, and reliably donning elastic gloves of any size without the aid of an assistant;

(b) to provide a device that requires no electrical, vacuum, nor air supply to inflate and maintain an elastic glove in an inflated state;

(c) to provide a device that can detect pinhole size voids in the glove material; and (d) to provide a device capable of functioning properly regardless of altitude or barometric pressure without adjustment of any kind.

Further objects and advantages are to provide a glove donning and leak detection device which is easy to use and is inexpensive to manufacture, which is mountable to virtually any flat surface and requires no adjustment or maintenance, which looks suitably attractive for use in a medical or dental office environment, which may be made from a variety of relatively inexpensive materials and may be used in sterile environments when made from high heat resistant materials. Still further objects and advantages will become apparent from a consideration of the ensuing description and drawings.

DRAWING FIGURES

REFERENCE NUMERALS IN DRAWINGS

| | | |
|---|---|---|
| 10 glove donning apparatus | 100 glove holding cylinder | 110 hand insertion opening |
| 120 groove | 130 upper edge | 200 mounting base |
| 210 valve mounting hole | 220 stand off spacers | 400 air check valve |
| 500 vacuum indicator tube | 510 seal | 530 reservoir |
| 540 mounting hole | 550 vent | 560 liquid level |

DESCRIPTION—FIGS. 1, 2, 3

Figure 1:
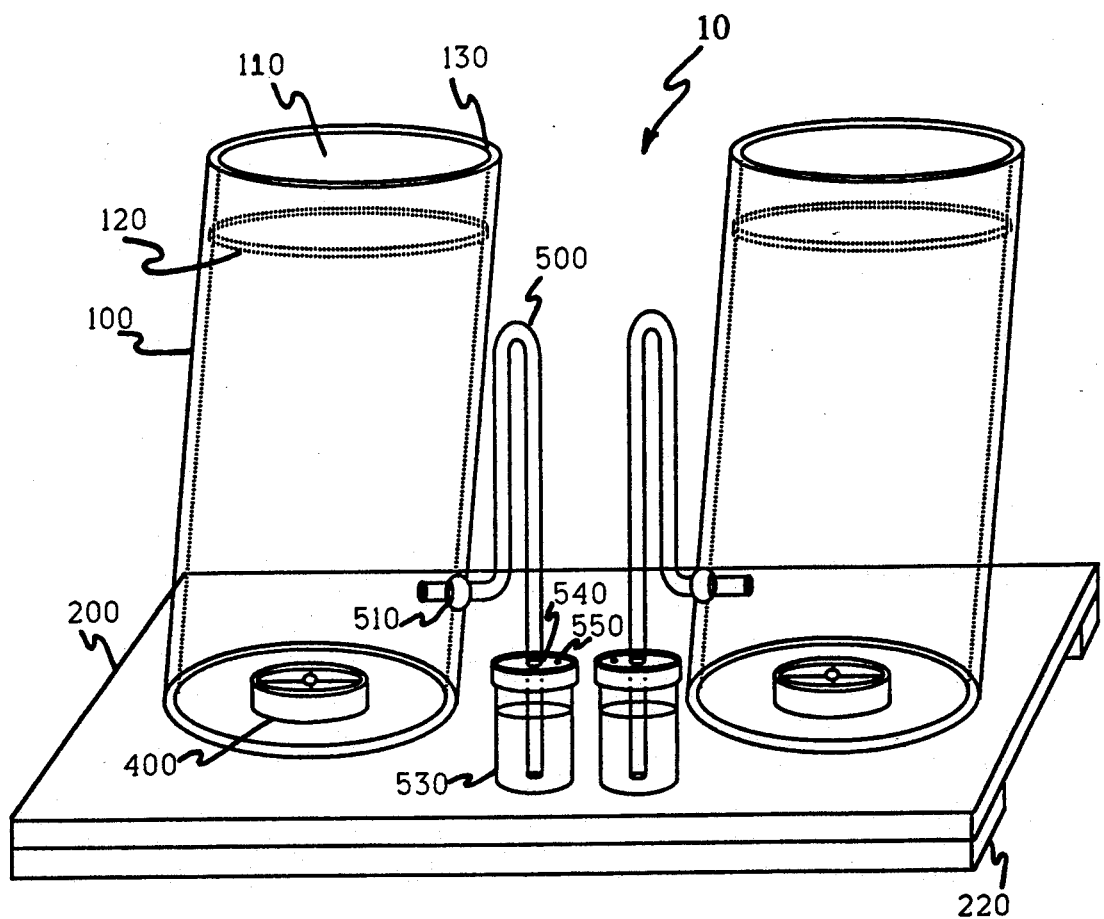
FIG. 1 shows a perspective view of the invention.
Figure 2:
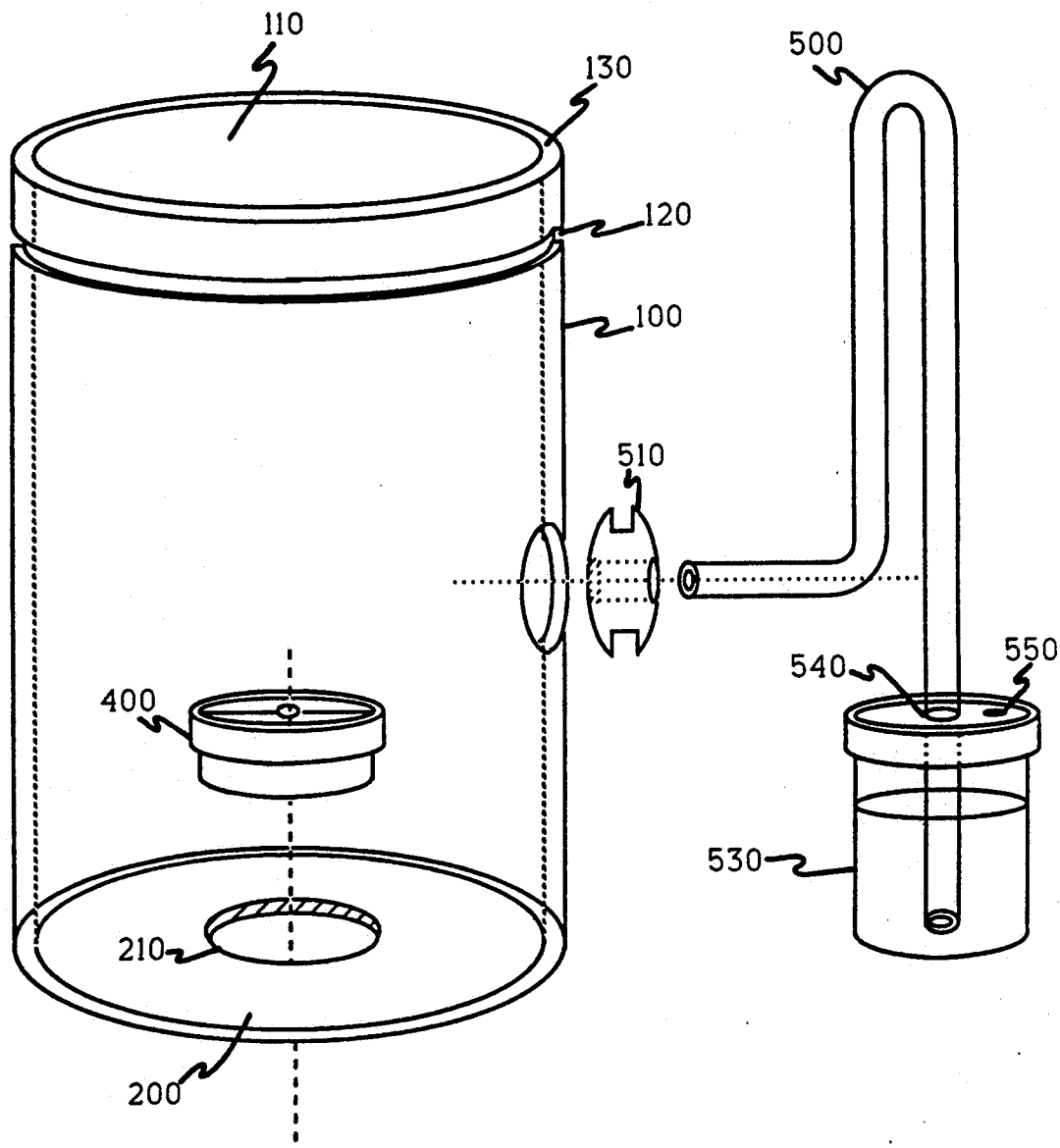
FIG. 2 shows a perspective "exploded" view of the parts of the device in FIG. 1.
Figure 3:
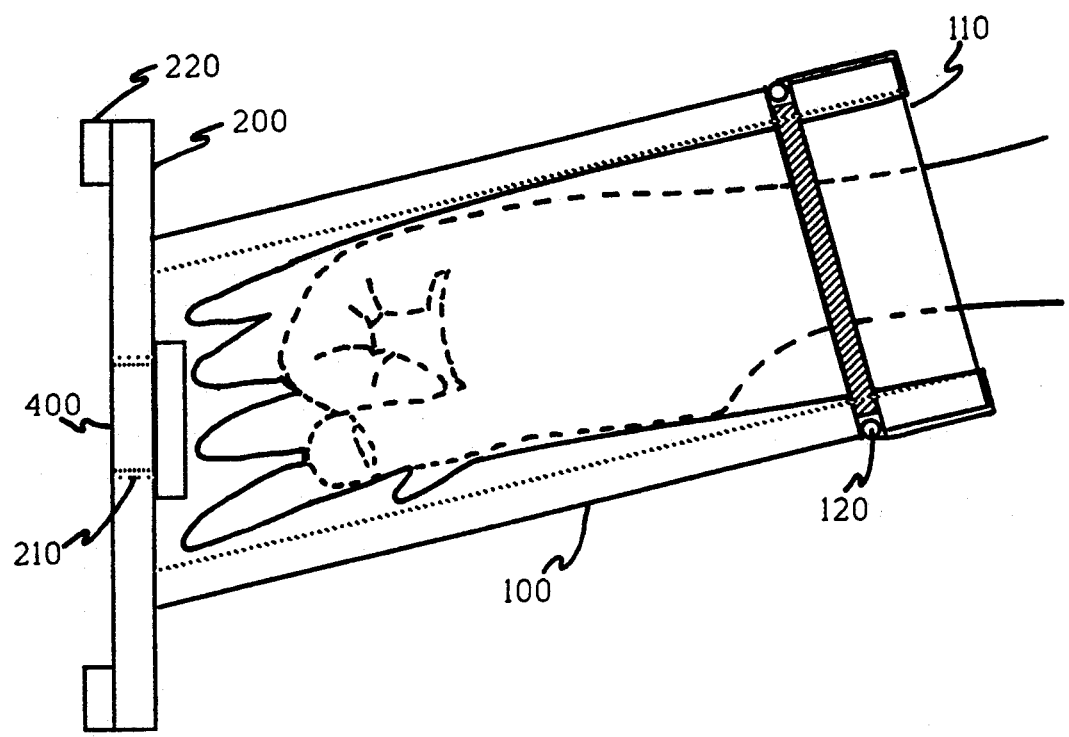
FIG. 3 shows a side view of the invention with glove mounted and being stretched by a hand.

A typical embodiment of a glove donning device 10 of the present invention is illustrated in FIG. 1 (perspective view), FIG. 2 (perspective "exploded" view) and FIG. 3 (side view). The description refers to a single cylinder, valve, groove, vacuum indicator and elastic glove whereas in practice, the invention would normally comprise two of each, constructed and mounted as mirror images of each other.

A glove holding cylinder 100 (FIG. 1 and FIG. 2) is preferably fabricated from rigid, thin-walled material such as plastic, glass, or metal tubing. The length of Cylinder 100 is typically 25 cm to 30 cm, with an inside diameter of approximately 11.5 cm. Cylinder 100 may be elliptically shaped to conform generally to the shape of the hand. Cylinder 100 is sealed at one end and has a hand insertion opening 110 at the opposite end. An upper edge 130 of cylinder 100 is polished smooth to prevent tearing or puncturing an elastic glove when the glove is stretched over opening 110. If a sterilized apparatus is required the device will be made entirely of high heat resistant material. A groove 120 (FIG. 2) approximately 0.15 cm deep circumscribes the exterior circumference of cylinder 100 near hand insertion opening 110.

A base 200 (FIG. 1 and FIG. 3) is preferably fabricated from rigid material such as plastic, glass or metal. In the preferred embodiment, base 200 also provides the air-tight closure for the closed end of cylinder 100. The angle formed at the junction of cylinder 100 and base 200 is offset from perpendicular by approximately 20 degrees (FIG. 3). This offset allows opening 110 to point generally upward toward the user when the device is wall mounted. The degree of upward tilt should be sufficient to allow the hand and finger portion of an elastic glove to fall easily, from gravity, into the interior of cylinder 100 when the apparatus is wall mounted. The junction between cylinder 100 and base 200 exists by either fusing cylinder 100 to base 200 or by molding cylinder 100 and base 200 as a single integrated unit. In either case, the union between cylinder 100 and base 200 is air-tight. Base 200 (FIG. 3) is used to secure the apparatus to a rigid surface such as wall or counter.

One end of a vacuum indicator tube 500 (FIG. 1 and FIG. 2) penetrates the wall of cylinder 100 through a seal 510. The other end of tube 500 is connected to a liquid reservoir 530 through a hole 540. A vent 550 on reservoir 530 allows the liquid in reservoir 530 to experiences atmospheric pressure. A liquid level 560 indicates the vacuum within cylinder 100.

In the preferred embodiment (FIG. 2) a valve mounting hole 210 in base 200 exists whereby a one-way air check valve 400 is mounted to allow air to flow from the interior of cylinder 100 to the ambient surroundings. Check valve 400 is mounted such that its air inlet communicates with the interior of cylinder 100 and its air outlet communicates with the ambient environment. The cross section of check valve 400 is approximately 2.5 cm. The junction between valve 400 and its mounting hole 210 is air-tight.

When the device is mounted to a surface, stand-off spacers 220 (FIG. 3) prevent the mounting surface from blocking the flow of air through check valve 400. These stand off spacers are unnecessary if valve 400 is mounted on cylinder 100 rather than on base 200.

OPERATION—FIGS. 3, 4

Figure 4:
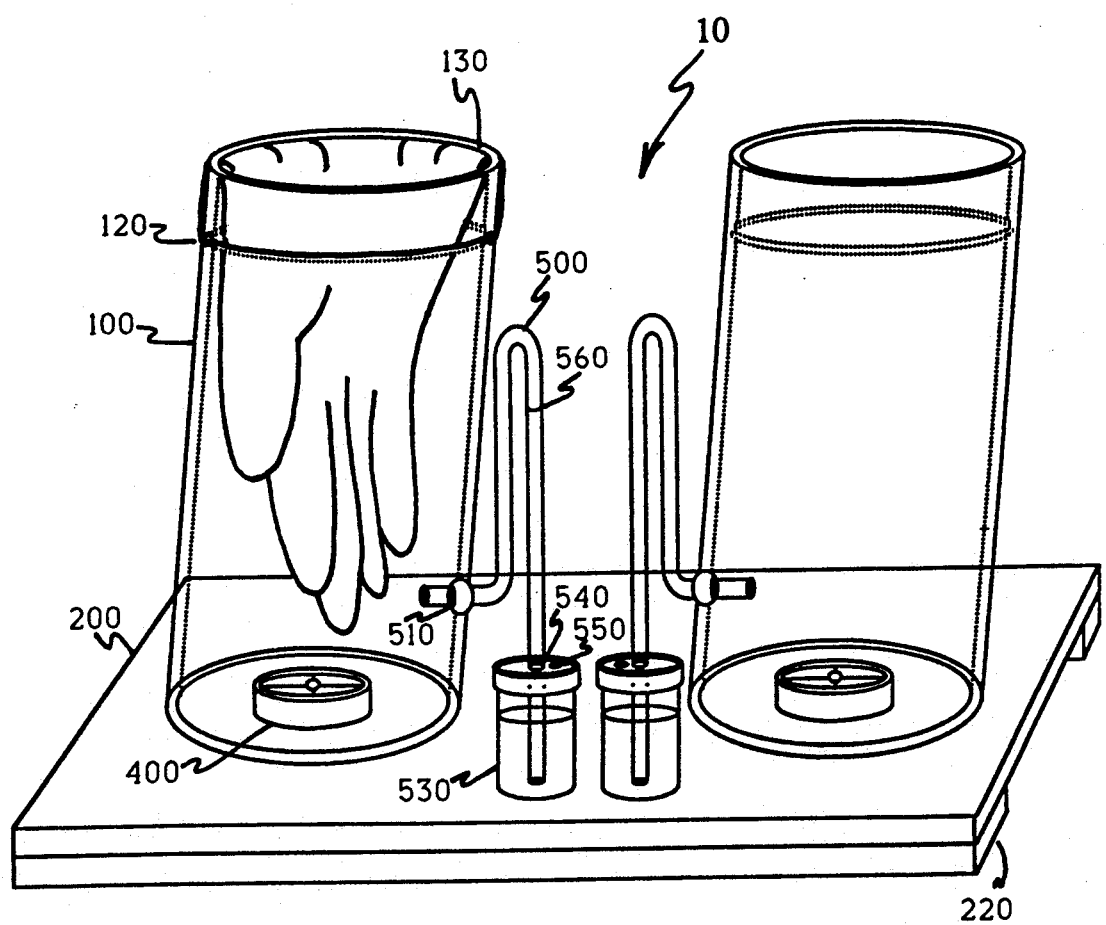
FIG. 4 shows a perspective view of the invention with elastic glove mounted and inflated.

To use the glove donning device, (FIG. 3 and FIG. 4) one lowers the hand and finger portion of an elastic glove into hand insertion opening 110. The elastic cuff is then stretched over opening 110 to engage it with cylinder 100. The cuff is then released over groove 120, whereby it seats into groove 120 due to the elasticity of the cuff. Once seated, groove 120 holds the cuff firmly to prevent its premature release and to improve the air-tightness between the glove and cylinder 100.

A hand, slightly closed to form a loose fist, is then inserted into the glove-covered opening 110 (FIG. 3). The hand is pushed well into cylinder 100 to stretch the elastic glove as far as possible. This action displaces the air below the glove forcing it out through valve 400. The hand is then retracted either partially or fully. As the glove attempts to return to its relaxed state, check valve 400 denies the entry of air into cylinder 100. Thus, the glove remains expanded (FIG. 4) due to the partial vacuum from below, and atmospheric pressure from above the elastic glove. The glove will remain expanded to a size much larger than a hand to facilitate hand insertion essentially friction free. With the glove expanded, the hand seats fully and easily into the glove without trapping air at the finger tips and without the need for adjustment.

To remove glove-covered hand from cylinder 100, use the free hand to roll the cuff out of groove 120 towards upper edge 130. As the cuff is rolled over edge 130, the air-tight seal is broken allowing air at atmospheric pressure to rush into cylinder 100 causing the glove to rapidly deflate and conform to the hand while simultaneously allowing the cuff to snap in place on the users wrist.

Additionally, the glove may be left expanded for a period of time before inserting a hand, as might happen when a technician prepares the device for later use by a dentist. During such time, the glove will deflate relatively soon if a hole exists in its elastic material. Deflation occurs as air passes through the hole and into cylinder 100, which equalizes the pressure difference above and below the glove.

Contaminated bodily fluids can pass through pinhole size voids so small, that the glove deflates too slowly to conveniently notice with the naked eye. To speed detection of such minute holes, a vacuum indicator tube 500 (FIG. 4) is used. One end of tube 500 is in communication with the vacuum developed within cylinder 100. The vacuum sucks colored liquid from reservoir 530 to a certain height depending on several factors well understood in the art. The greater the length of liquid used to indicate absolute vacuum, the easier it is to detect very small changes in this vacuum. If even a minute pinhole leak exists in the glove, liquid level 560 will fall noticeably and immediately. The drop in liquid level 560 is easily observable to the naked eye within seconds after removing the hand that inflated the glove. Conversely, if liquid level 560 remains steady after the hand is removed, it indicates the glove has integrity.

SUMMARY, RAMIFICATIONS, AND SCOPE

Accordingly, the reader will see that the glove donning device of this invention can be used to speed and ease the process of donning elastic gloves while quickly detecting very small pinhole size voids in the elastic material through which contaminated fluids can pass to the wearer. Furthermore, the device has the additional advantages in that the device may be prepared for use by one person for later use by another as might happen in a busy dentistry office or emergency room;

the device requires no electrical or pneumatic power source to operate;

the device is compact and light weight enough to be mounted on any flat surface in any orientation;

the device needs no connection to other equipment;

the device requires no maintenance or adjustment;

the device is easy and inexpensive to manufacture.

Although the description above contains many specificities, these should not be construed as limiting the scope of the invention but as merely providing illustrations of some of the presently preferred embodiments of this invention. For example, the glove holding cylinders can have many different cross sectional shapes, such as elliptical, square, rectangular, etc.; the length and diameter of the glove holding cylinders may vary considerably from those described; the method for closing the sealed end of the cylinder may be accomplished using a flat plate, a molded-in bottom, a flexible cover, etc.; the valve used to pass air from within the cylinder to the ambient surroundings may take the form of any number of one-way air check valves such as diaphragmed ports, duck bill valves, ball cock, spring loaded sealing ports, etc.; the mounting of the one way air check valve may be accomplished by mounting to the base, the cylinder wall, or an additional tube inserted into same, etc.; the method used to detect small changes in vacuum pressure within the cylinder may be accomplished by using a column of any visible liquid in a tube of various length and shape, by standard vacuum pressure meters, materials that change color or sound alarms when pressure changes occur, mounting the device may be accomplished using a mounting base, a bracket and clamp that attaches to the cylinders, snap type clamps that allow easy removal and remounting of cylinders to ease the sterilization process when necessary, etc.

Thus the scope of the invention should be determined by the appended claims and their legal equivalents, rather than by the examples given.

I claim:

1. A device to hold, expand, and detect pinhole voids in, elastic gloves, comprising: in combination, an essentially cylindrical chamber having an air tight closure means at one end, a hand insertion opening at the opposite end, and a glove holding means formed on an exterior circumference of the chamber, an air check valve interposed between the interior of the chamber and the ambient surroundings, and an analog vacuum indicator in communication with the interior of the chamber wherein said analog vacuum indicator includes a display tube connected to a liquid reservoir wherein a vacuum condition can be displayed in a analog fashion by the analog type vacuum indicator.

2. A device as recited in claim 1 wherein said essentially cylindrical chamber is provided by, a thin walled, elongated, rigid tube.

3. A device as recited in claim 2 wherein the tube is constructed of clear plastic tubing having an outside diameter greater than the unstretched wrist diameter of said elastic glove and having a length greater than the finger and palm portion of said elastic glove.

4. A device as recited in claim 1 wherein said glove holding means is provided by a groove formed on the exterior circumference of the chamber within approximately 4 centimeters of said hand insertion opening, said groove having a depth sufficient to hold the wrist portion of the glove firmly in place while allowing the wrist portion when seated in said groove to be easily rolled out of said groove whereby the glove may be removed from the chamber.

5. A device as recited in claim 1 wherein said air tight closure means is provided by a thin, rigid, planner member bonded to the chamber to form an air tight seal with one end of the chamber and having length and width dimensions greater than the outside dimensions of the chamber.

6. A device as recited in claim 5 wherein said thin, rigid, planner member is constructed of plastic approximately 6 millimeters thick.

7. A device as recited in claim 5 wherein said thin, rigid, planner member extends radially beyond the dimensions of the chamber approximately 3 centimeters whereby said rigid planner member provides a mounting means whereby said mounting means with the chamber attached can be wall mounted.

8. A device as recited in claim 1 wherein a hole is provided through the part of said air tight closure means located in an area encircled by the inside diameter of the chamber, providing a mounting means for said air check valve.

9. A device as recited in claim 1 wherein said air check valve is provided by an elastomeric diaphragm valve interposed between the chamber and the ambient atmosphere, having the valve's intake port in first communication with the interior of the chamber and the valve's exit port in first communication with the ambient atmosphere, wherein the valve allows air within the chamber to be forced out of the chamber to ambient surroundings while denying air entry into said chamber.

10. A device as recited in claim 9 wherein said elastomeric diaphragm valve is provided by, in combination an essentially circular elastomeric diaphragm type valve center mounted to a ported, rigid valve seat.

11. A device as recited in claim 1 wherein said display tube of said analog vacuum indicator includes a horizontal portion in first communication with the interior of the chamber and a vertical portion in communication with said liquid reservoir wherein small changes in vacuum caused by pinhole voids in the glove are magnified by a large change in liquid movement within said display tube due to the change in pressure.

12. A device as recited in claim 1 wherein, an extension of said display tube passes through an elastomeric seal interposing the interior and exterior of the chamber allowing said extension to be rotated within the seal while maintaining air tightness, enabling said display tube to be inclined from the vertical position thus creating an elongated liquid level display for any given static vacuum wherein an analog change in vacuum is displayed over a longer distance to magnify small changes in vacuum.

13. A device as recited in claim 1 wherein said display tube is constructed of clear plastic.

14. A device to facilitate holding, expanding, and detecting pinhole voids in an elastic glove within a chamber comprising, in combination, a holding means integrated with said chamber to hold said elastic glove over an opening in said chamber, an air control means for evacuating air from said chamber when a displacing means is inserted into said chamber, and a display means to display a change in vacuum within said chamber, said elastic glove having a mounting portion of such dimensions as to exert a compression force on the entire outside dimension of said holding means of said chamber wherein an air tight seal is maintained during expansion and inflation of said elastic glove, said chamber including an essentially cylindrical, thin walled, elongated, rigid tube with a closure means on one end and the opposite end of the tube defining the opening to the rigid tube, and said holding means comprising a groove formed on an exterior circumference of the tube, within approximately four centimeters of said opening, to hold said elastic material firmly in place over said opening in such a manner that when a vacuum is created in the tube, said elastic material is pulled into the tube and inflated, said closure means comprising a rigid planner member having an air tight seal with one end of the tube and extending radially beyond the outside dimensions of the tube an amount sufficient to use said rigid planner member as a mounting means so that said chamber can be wall mounted, said air control means comprising, a one way air check valve including an essentially circular elastomeric diaphragm valve, center mounted to a ported, rigid valve seat mounted to interpose between said chamber and the ambient atmosphere, having the intake port in communication with the interior of said chamber and the exit port in first communication with the ambient atmosphere, wherein the valve's one way action allows air within said chamber to be forced out of said chamber to ambient surroundings while denying air entry into said chamber, said displacing means comprising, in combination, said elastic glove stretched over said opening to said chamber to form an air tight seal and an object, similar but smaller in outside dimension than the inside dimension of said opening, pushed into the elastic glove covered chamber wherein air in said chamber is displaced and forced through said one way air check valve to ambient surroundings, said display means comprising, a transparent, elongated display tube having approximately three millimeters inside diameter and a liquid reservoir, having one end of the display tube in communication with the interior of said chamber and the opposite end in first communication with said liquid reservoir, wherein a vacuum developed within said chamber sucks liquid from the reservoir into the display tube to display, in analog fashion, both static vacuum and minute changes in said vacuum.

15. A method to inflate, hold and detect leaks in an unpackaged elastic glove comprising the steps of, stretching the wrist portion of the glove over an end of a cylinder having inside dimensions large enough to allow easy entry of a human hand, the opposite end of said cylinder having an air tight closure, and then releasing the wrist portion of the glove into a groove formed on an exterior circumference of said cylinder approximately four centimeters from the open end of said cylinder, so that the elastic contracts and seats into the groove to improve holding friction and air tightness between the glove and said cylinder, and then inserting said human hand, held as a loose fist to act as a piston, into the glove covered cylinder thereby stretching the glove and displacing air within said cylinder by forcing the displaced air to exit said cylinder through a passively operated air check valve interposed between the interior of said cylinder and the ambient surroundings, and whereby the air attempting to enter said cylinder through said passively operated air check valve causes the valve to close, denying air entry to said cylinder, creating a partial vacuum within said cylinder which sucks the glove into said cylinder where it is held inflated by atmospheric pressure on one side of the glove and a partial vacuum on the opposite side, to allow easy entry of the hand, and then retracting said human hand from cylinder;

then observing the change, in the level of liquid sucked into a transparent vacuum display tube having one end of the display tube in first communication with the vacuum created within said cylinder and the opposite end of the display tube in first communication with a liquid reservoir, the vacuum generated in said cylinder pulling liquid from the reservoir into the transparent tube to display, in analog fashion by a changing liquid level, a change in vacuum as would occur if the glove contained a pinhole size void.

* * * * *